(12) United States Patent
Takeuchi

(10) Patent No.: US 10,377,115 B2
(45) Date of Patent: Aug. 13, 2019

(54) METHOD OF MANUFACTURING STRETCHABLE SHEET

(71) Applicant: Daio Paper Corporation, Ehime (JP)

(72) Inventor: Tomonari Takeuchi, Tochigi (JP)

(73) Assignee: DIAO PAPER CORPORATION, Ehime (JP)

( * ) Notice: Subject to any disclaimer, the term of this patent is extended or adjusted under 35 U.S.C. 154(b) by 120 days.

(21) Appl. No.: 15/546,939

(22) PCT Filed: Jan. 29, 2016

(86) PCT No.: PCT/JP2016/052811
§ 371 (c)(1),
(2) Date: Jul. 27, 2017

(87) PCT Pub. No.: WO2016/121981
PCT Pub. Date: Aug. 4, 2016

(65) Prior Publication Data
US 2018/0015709 A1    Jan. 18, 2018

(30) Foreign Application Priority Data

Jan. 30, 2015 (JP) ................... 2015-017498
Mar. 27, 2015 (JP) ................... 2015-067324
(Continued)

(51) Int. Cl.
B32B 37/00 (2006.01)
B32B 38/00 (2006.01)
(Continued)

(52) U.S. Cl.
CPC .......... B32B 37/0053 (2013.01); A61F 13/15 (2013.01); A61F 13/15699 (2013.01);
(Continued)

(58) Field of Classification Search
CPC ..... B32B 37/00; B32B 37/005; B32B 37/005; B32B 37/0053; B32B 37/06; B32B 38/00;
(Continued)

(56) References Cited

U.S. PATENT DOCUMENTS 6,572,595 B1    6/2003 Klemp et al.
2010/0051170 A1    3/2010 Nakakado
(Continued)

FOREIGN PATENT DOCUMENTS

JP    10-029259 A    2/1998
JP    2004532758    10/2004
(Continued)

*Primary Examiner* — Jacob T Minskey
*Assistant Examiner* — Matthew Hoover
(74) *Attorney, Agent, or Firm* — Muncy, Geissler, Olds & Lowe, P.C.

(57) ABSTRACT

To acquire a stretchable sheet having air permeability due to the presence of through-holes, with no hole formed through outer layers.
There are provided: interposing a resilient film (30) that stretches and contracts, in a stretched state between a first sheet layer (21) having no elasticity and a second sheet layer (22) having no elasticity; and joining the first sheet layer (21) and the second sheet layer (22) together with a number of joints directly or through the resilient film by melting the resilient film (30) with ultrasonic fusion energy applied by a thermal fusion device from the outside of the first sheet layer (21) and the outside of the second sheet layer (22) to a number of joint regions with intervals, during the interposing. The resilient film (30) is supplied around a counter roll (63) so as to be supplied around the anvil roll (60), and the anvil roll (60) is accelerated to be faster than the counter roll (63) in peripheral speed to stretch the resilient film (30).

7 Claims, 16 Drawing Sheets

(30) Foreign Application Priority Data

| Mar. 27, 2015 | (JP) | 2015-067325 |
| Mar. 30, 2015 | (JP) | 2015-068068 |
| Mar. 30, 2015 | (JP) | 2015-070295 |
| Sep. 30, 2015 | (JP) | 2015-195461 |
| Nov. 10, 2015 | (JP) | 2015-220312 |

(51) Int. Cl.
- *A61F 13/00* (2006.01)
- *A61F 13/496* (2006.01)
- *A61F 13/15* (2006.01)
- *B32B 37/06* (2006.01)
- *B32B 38/18* (2006.01)

(52) U.S. Cl.
CPC ...... *A61F 13/15739* (2013.01); *A61F 13/496* (2013.01); *B32B 37/06* (2013.01); *B32B 38/18* (2013.01); *B32B 2307/51* (2013.01); *B32B 2310/028* (2013.01); *B32B 2555/02* (2013.01)

(58) Field of Classification Search
CPC ......... B32B 38/10; B32B 38/18; A61F 13/00; A61F 13/10; A61F 13/15; A61F 13/15; A61F 13/156; A61F 13/156; A61F 13/1569; A61F 13/15699; A61F 13/157; A61F 13/1573; A61F 13/15739; A61F 13/49; A61F 13/49; A61F 13/496
See application file for complete search history.

(56) References Cited

U.S. PATENT DOCUMENTS

| 2010/0215923 A1* | 8/2010 | Frost | B32B 27/32 |
| | | | 428/196 |
| 2011/0319853 A1 | 12/2011 | Yamashita et al. | |
| 2014/0130956 A1* | 5/2014 | Floberg | B32B 5/022 |
| | | | 156/73.5 |
| 2017/0087029 A1* | 3/2017 | Nelson | B32B 7/05 |
| 2018/0028371 A1 | 2/2018 | Takaishi | |

FOREIGN PATENT DOCUMENTS

| JP | 2008295838 A | 12/2008 |
| JP | 4508885 B2 | 7/2010 |
| JP | 2010195044 A | 9/2010 |
| JP | 2010200974 A | 9/2010 |
| JP | 4562391 B | 10/2010 |
| JP | 4934835 B2 | 5/2012 |
| JP | 2014-520589 | 8/2014 |
| JP | 2014150917 A | 8/2014 |
| JP | 2016140477 A | 8/2016 |
| JP | 2016185265 A | 10/2016 |
| JP | 6383712 B | 8/2018 |
| WO | WO03000165 A1 | 1/2003 |
| WO | WO2008126708 A1 | 10/2008 |
| WO | WO2011048512 A2 | 4/2011 |
| WO | WO2013002691 A1 | 1/2013 |
| WO | WO2015168032 A1 | 11/2015 |

* cited by examiner

JOINT AREA RATE

A<C=D

AFTER STRETCHING

STRETCHING STRESS

A>C=D

METHOD OF MANUFACTURING STRETCHABLE SHEET

TECHNICAL FIELD

The present invention relates to a method of manufacturing a stretchable sheet including a resilient film interposed between a first sheet layer and a second sheet layer.

BACKGROUND ART

Elasticity is typically added to proper positions, such as legs and a waist, in an absorbent article, for example, a disposable diaper in order to improve a fit to the surface of a body. Conventionally, a technique of securing an elongated resilient and elastic member, such as a rubber thread, that has stretched in a longitudinal direction, has been widely adopted as an exemplary technique of adding elasticity. In a case where elasticity is added with a degree of width, a mode of securing rubber threads arranged with intervals in a width direction, has been adopted.

Meanwhile, a stretchable sheet having a nonwoven fabric/ elastomeric film/nonwoven fabric structure, has been proposed in consideration of performing pressing to an elongated face to add elasticity in addition to texture, instead of the plurality of rubber threads arranged in parallel (e.g., Patent Literature 1).

Patent Literature 1 discloses a porous mode in which a hole that penetrates through the entirety of a first outer layer, a second outer layer, and a resilient film (an elastomer), is formed, in addition to a nonporous mode in which no hole is formed through the entirety of the first outer layer, the second outer layer, and the elastic film.

In a case where the stretchable sheet in the nonporous mode is used, for example, as a sheet included in the back surface of a disposable diaper, there is a problem that stuffiness occurs due to no air permeability.

Meanwhile, in the porous mode in Patent Literature 1, the resilient film that is continuous and stretches and contracts in a machine direction (MD) is supplied between the first outer layer and the second outer layer, the elastic film having a melting point higher than those of the outer layers or no melting point, and then the first outer layer and the second outer layer are directly joined together by welding at a predetermined position. After that, tensile force acts in a CD direction to form a through-hole penetrating through the entirety of the first outer layer, the resilient film, and the second outer layer, at a joined site, so that air permeability is secured.

In any case, when the resilient film (the elastomer) stretches in the machine direction, a so-called neck-in phenomenon in which the width of the resilient film shortens, occurs. The resilient film having a width wider than the respective widths of the first outer layer and the second outer layer, is required to be prepared in order to acquire a laminated film having a desired width with the occurrence of the neck-in, resulting in the high cost of materials.

A phenomenon in which there is a difference in stretching and contracting stress between the center in a width direction and both side portions in the width direction, occurs in the CD direction of the sheet to be laminated in practice, together with the neck-in of the resilient film. In a case where the stretchable sheet that has been laminated is applied to a product, for example, a disposable diaper, a problem may occur that uniform stress may not be acquired.

CITATION LIST

Patent Literature

Patent Literature 1: JP 4562391 B2

SUMMARY OF INVENTION

Technical Problem

A main object of the present invention is to provide a method of manufacturing a stretchable sheet, capable of suppressing neck-in to reduce material costs.

Solution to Problem

The present invention that has solved the problem, is as follows:
(Primary Mode)
A method of manufacturing a stretchable sheet that stretches and contracts, according to the present invention, includes: interposing a resilient film that stretches and contracts, in a stretched state between a first sheet layer having no elasticity and a second sheet layer having no elasticity; and joining the first sheet layer and the second sheet layer together with a number of joints directly or through the resilient film by melting the resilient film with ultrasonic fusion energy applied by a thermal fusion device from an outside of the first sheet layer and an outside of the second sheet layer to a number of joint regions with intervals, in a state where the resilient film has been interposed in the stretched state between the first sheet layer and the second sheet layer, during the interposing. The thermal fusion device includes an anvil roll and an ultrasonic horn. A number of protruding portions are formed with intervals in a roll length direction and in an outer circumferential direction on an outer surface of the anvil roll. A counter roll is arranged to face the anvil roll. The resilient film is supplied around the counter roll so as to be supplied around the anvil roll, and the anvil roll is accelerated to be faster than the counter roll in peripheral speed to stretch the resilient film and additionally a group of the protruding portions of the anvil roll and the ultrasonic horn performs the joining.

The stretchable sheet according to the present invention, includes no hole formed through the first sheet layer and the second sheet layer. Regarding this point, the stretchable sheet is different from a stretchable sheet illustrated in FIG. 5 or 7 in JP 4562391 B2.

Meanwhile, providing the resilient film in the stretched state in a machine direction to a position at which the joining is performed, can form a through-hole through at least a boundary portion in the machine direction between the resilient film and each of the joints. The reason why the through-holes are formed, will be described in detail later.

The thermal fusion device includes a unit including the anvil roll and the ultrasonic, the unit configured to at least partially melt at least one layer of the first sheet layer, the second sheet layer, and the resilient film, with the energy to be applied.

It is considered that the unevenness of the group of the protruding portions of the anvil roll resists traveling force that causes neck-in together with the stretch of the resilient film, the traveling force acting to the center in a width direction, so as to suppress the neck-in.

Since the resilient film is supplied around the counter roll so as to be supplied around the anvil roll, thus it is considered that the resistance between the resilient film and the surfaces of the rolls also suppresses the neck-in.

The counter roll preferably is a nip roll which constitutes a nip stage together with the anvil roll. The resilient film is preferably supplied around the anvil roll through the nip stage.

It is considered that the presence of the nip stage further strengthens the resistance between the resilient film and the surfaces of the rolls so as to contribute to the suppression of the neck-in.

Accelerating the anvil roll to be faster than the nip roll in peripheral speed, can stretch the resilient film.

The distance between the nip stage and a position at which the resilient film separates from the anvil roll, preferably is 250 mm or less.

The anvil roll preferably is a crowned roll instead of a flat roll. It is considered that providing the crowned roll strengthens the resistance between the resilient film and the surface of the crowned roll so as to contribute to the suppression of the neck-in.

An exemplary arrangement of the joints has a staggered pattern.

When the anvil roll is viewed in a developed state, the protruding area rate of the total area of the group of the protruding portions included in a unit area, preferably varies at least in roll length.

Meanwhile, providing the resilient film in the stretched state in the machine direction to the position at which the joining is performed, can form the through-hole through at least the boundary portion in the machine direction between the resilient film and each of the joints.

The following exemplary joining modes may be provided for the joints according to the present invention.
(1) A mode in which the first sheet layer and the second sheet layer partially melt to join the resilient film together, namely, the first sheet layer and the second sheet layer are joined together through the resilient film.
(2) A mode in which the resilient film melts so as to make a transition into the first sheet layer and the second sheet layer so that the first sheet layer and the second sheet layer are directly joined together without the resilient film.
(3) A mode in which both surface regions of the resilient film melt to make a transition into the first sheet layer and the second sheet layer, but the resilient film partially remains so that the first sheet layer and the second sheet layer are jointed together through the remaining resilient film, the mode being intermediate between the mode (1) and the mode (2).

Particularly, a difference occurs in resilient film strength between the joints and non-joints in the mode (2) and the mode (3) among the modes. Therefore, breaking occurs at the boundary portion between each joint and each non-joint when stretching is performed mechanically or manually in the stretching and contracting direction: after a product is made with the stretchable sheet contracted by temporarily releasing the stretched state in which the stretchable sheet has stretched; or after a product is made with the stretchable sheet contracted by temporarily releasing the stretched state after the stretchable sheet that has stretched is joined to a different member.

As a result, the through-holes are formed.

The formation of the through-holes has the advantage of securing air permeability. The through-holes are not necessarily required to be formed to all the joints, and thus forming the through-holes to some joints also indicates air permeability. In a case where the resilient film can stretch and contract only in the machine direction, the through-holes each have a shape stretched from the edge of the joint in the machine direction. In a case where the resilient film can stretch and contract in both the machine direction (MD) and a direction orthogonal to the machine direction (e.g., a CD direction), the through-holes each have a shape stretched from the edge of the joint in both directions and, in some cases, may have an annular shape around the joint.

As previously described, the resilient film according to the present invention, includes an elastomer in general so as to be able to stretch and contract in the machine direction (MD) and in the orthogonal direction (CD).

The joints having no directivity, such as a circle, are provided or the joints each having a length in the orthogonal direction (the width direction: CD) longer than a length in the machine direction (MD), are provided.

In order to perform the method according to the present invention, the melting point of the resilient film is preferably approximately 80 to 145° C., the melting points of the first sheet layer and the second sheet layer are preferably approximately 85 to 190° C., particularly preferably approximately 130 to 190° C., and the difference between the melting points of the first sheet layer and the second sheet layer and the melting point of the resilient film being lower is preferably approximately 50 to 80° C.

As a preferred specific example, the melting point of the resilient film is 95 to 125° C., the melting point of the first sheet layer is more than 125° C. to 160° C., more preferably 130 to 160° C., and the melting point of the second sheet layer is more than 125° C. to 160° C., more preferably 130 to 160° C.

When the anvil roll is viewed in the developed state, the protruding area rate of the total area of the group of the protruding portions included in the unit area, preferably varies at least in roll length.

The protruding portions correspond to the joints. As a preferred example of the joints, the area of each of the joints is 0.14 to 3.5 mm$^2$. The area rate of the joints is preferably 1.8 to 22.5%.

The area rate of the joints in an elastic region is 1.8 to 22.5%.

Here, the "area rate" means the ratio of an object portion per unit area, and the total area of the object portion (e.g., the joints and the openings of the through-holes) in an object region (e.g., the elastic region), divided by the area of the object region, is expressed in percentage. In particular, the "area rate of the joints" means an area rate in a state where the object region has stretched up to an elastic limit.

The area of the opening of each of the through-holes in a natural length state of the stretchable sheet, is preferably from more than 1 time to 1.5 times the area of each of the joints.

The area of the opening of each of the through-holes means a value in a state where the stretchable structure has had a natural length, and means a minimum value in a case where the area of the opening of each of the through-holes is nonuniform in a thickness direction, such as nonuniformity between the front and back of the resilient film.

The joint area rate in the present specification, can be selected by determining the protruding portions of the anvil roll in size, shape, space interval, arrangement pattern in the roll length direction and the roll circumferential direction, to be described later.

"Stretching stress" to be described later means "stress (N/35 mm) in performing stretching up to 50% of the elastic limit" measured in a tensile test having an initial chuck interval (a reference inter-line distance) of 50 mm and a tensile speed of 300 mm/min conforming to JIS K7127:

1999 "Plastics-Determination of tensile properties". In a case where a test piece having a width of 35 mm may not be cut out, the test piece having a width that can be cut out is prepared and then a value including a measured value converted into the width of 35 mm, is used. In a case where an object region is small and no sufficient test piece may be extracted, as long as comparison in stretching and contracting stress is made, even a small test piece can be at least compared appropriately.

In an embodiment to be described later, in a case where a region includes different pieces of stretching stress, there is the problem of how to extract test pieces for verifying a difference in elastic force. In this case, for comparison in stretching and contracting stress, a test piece is extracted for each site of the stretchable sheet, and then the test pieces can be compared in magnitude with the stress when a length of 100% in a natural state is stretched to a length of 150%, instead of acquiring an absolute value in stretching and contracting stress.

Advantageous Effects of Invention

As described above, according to the present invention, the method of manufacturing the stretchable sheet, is capable of suppressing the neck-in to reduce the material costs.

DESCRIPTION OF EMBODIMENTS

An embodiment of the present invention will be described in detail below with reference to the attached drawings.

A stretchable sheet according to the present invention can be used for an absorbent article, such as a disposable diaper, a sanitary napkin, or an absorbent pad, that absorbs and retains a body fluid.

As illustrated in FIGS. 5 to 8, the stretchable sheet includes a resilient film 30 stretchable and contractible in front-back directions, laminated between a first sheet layer 21 including a nonwoven fabric having no elasticity and a second sheet layer 22 including a nonwoven fabric having no elasticity, the first sheet layer 21 and the second sheet layer 22 being joined together with a number of the bond portion 40 with intervals directly or through the resilient film 30.

Here, the "having no elasticity" of each of the first sheet layer 21 and the second sheet layer 22 does not mean completely no stretch and contraction but substantially no stretch and contraction for comparison in the degree of the elasticity of the resilient film 30.

Figure 9:
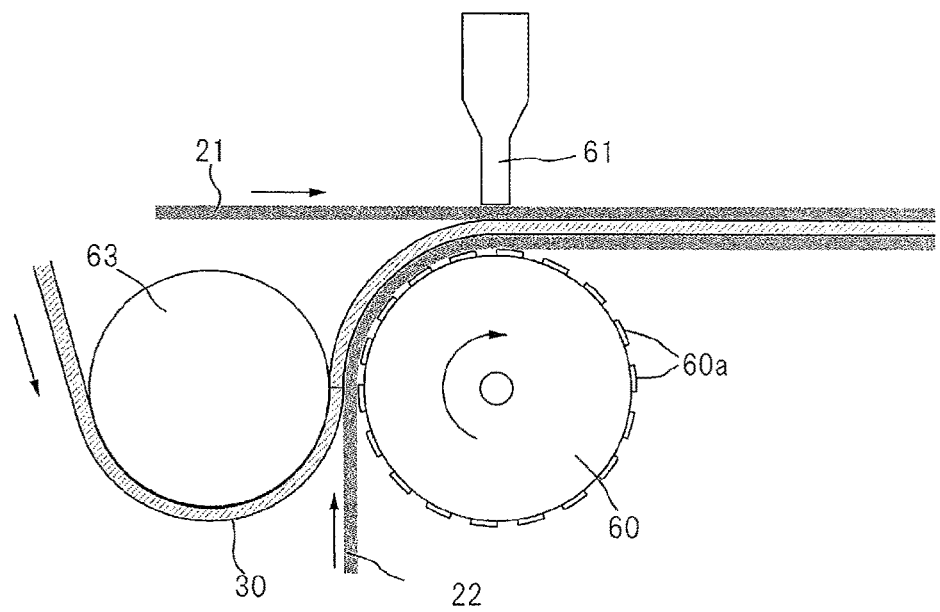
FIG. 9 is a schematic view of exemplary joining according to the present invention.

In the joining, as illustrated in FIG. 9, the first sheet layer 21, the resilient film 30, and the second sheet layer 22 are supplied between an anvil roll 60 including protruding portions 60a formed on an outer surface in a predetermined pattern, and an ultrasonic horn 61. Then, the ultrasonic horn 61 applies ultrasonic fusion energy to melt mainly the resilient film 30 so that the first sheet layer 21 and the second sheet layer 22 are joined together.

A counter roll 63 is arranged so as to face the anvil roll 60. The counter roll 63 preferably is a nip roll that nips the resilient film 30 between the anvil roll and the counter roll 63.

In a structure of the device, the resilient film 30 is supplied around the counter roll (the nip roll) 63 so as to reach a nip position and then the resilient film 30 is supplied around the anvil roll 60.

At that time, the peripheral speed of the anvil roll 60 driven to rotate, is accelerated to be faster than the peripheral speed of the counter roll (the nip roll) 63 so that a group of the protruding portions 60a of the anvil roll 60 and the ultrasonic horn 61 perform the joining with the resilient film 30 stretched.

At this time, selecting a speed difference for accelerating the peripheral speed of the anvil roll 60 to be faster than the peripheral speed of the nip roll 63, can set a stretch rate (a length is defined as 100% in a natural state as a reference) in a manufacturing process of the resilient film 30.

Figure 10:
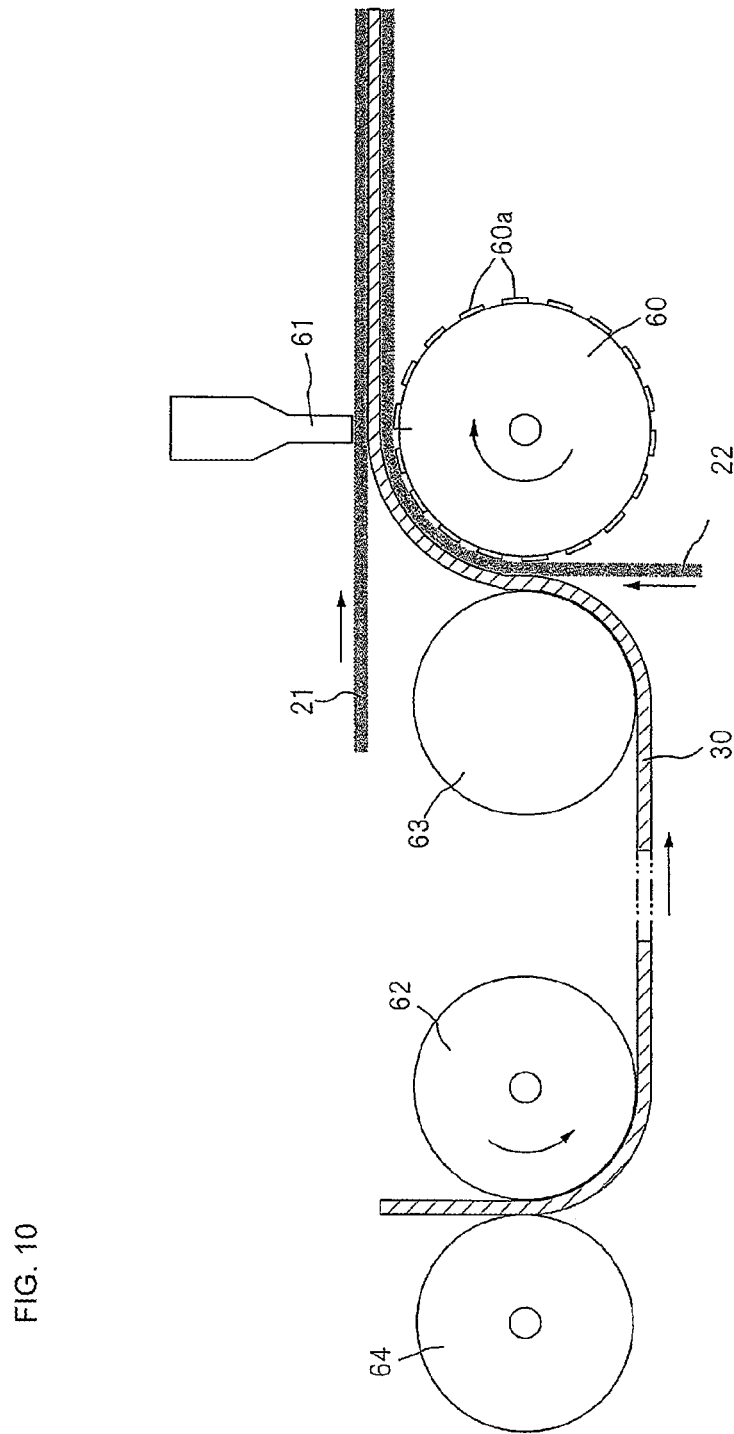
FIG. 10 is a schematic view of a stretching unit of a resilient film according to a comparative example.

Note that, as illustrated in FIG. 10, the peripheral speed of the anvil roll 60 driven to rotate is accelerated to be faster than the peripheral speed of a driving roll 62 behind so that the resilient film 30 can stretch with the speed difference between the rolls. A guide roller 64 is provided.

However, the anvil roll 60 driven to rotate and the driving roll 62 are spaced apart from each other, and large neck-in occurs between the rolls.

Figure 11:
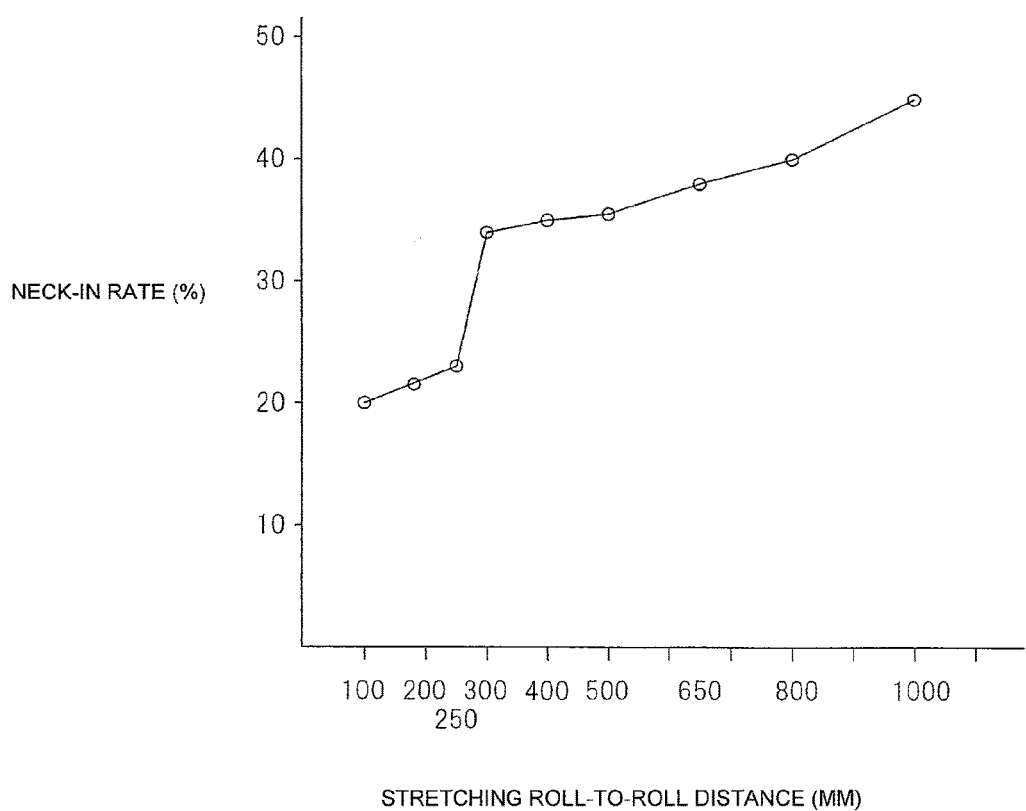
FIG. 11 is a graph of an experimental result of neck-in generation.

FIG. 11 illustrates an examined result of the relationship between roll-to-roll spaced distance and neck-in rate.

From FIG. 11, the neck-in rate rapidly increases when a stretching roll-to-roll distance of 250 mm or more is provided, instead of simply increasing in direct-proportion to the stretching roll-to-roll distance. Therefore, in the example illustrated in FIG. 9, the distance from the tangent of the resilient film 30 to the counter roll (the nip roll) 63 to a position at which the resilient film 30 separates from the anvil roll 60, is preferably 250 mm or less. Particularly, the distance is preferably 180 mm or less.

Figure 12:
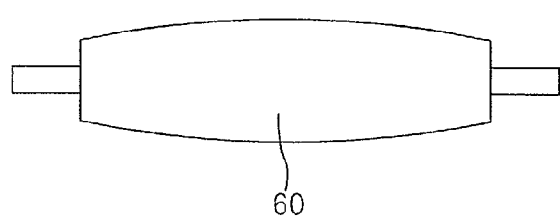
FIG. 12 is an explanatory view of a crowned roll.

The anvil roll 60 preferably is a crowned roll illustrated in FIG. 12. The length of the anvil roll 60 is preferably approximately 1000 mm.

A crowning amount can be appropriately selected, and as necessary roll end portions are cooled so that the crowning amount can be adjusted.

Meanwhile, the protruding portions 60a of the anvil roll 60 can be formed to be dense toward the center in roll length. Thus, with the mode, a center portion thermally expands at a maximum so that a crown is easily added.

Meanwhile, the material of the anvil roll 60 preferably is die steel, and the hardness of hardening is optimally 60 to 61 in HRC.

Figure 6:
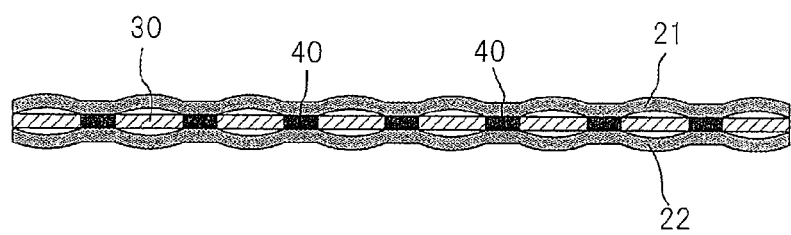
FIG. 6 is a sectional view for describing the stretchable sheet in a joined state.
Figure 7:
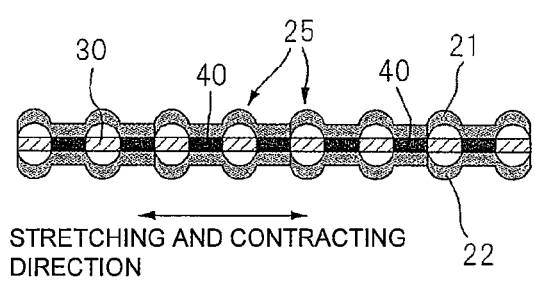
FIG. 7 is a sectional view for describing the stretchable sheet in a contracted state.

FIG. 6 schematically illustrates a section of the stretchable sheet in a stretched state after the joining (note that, no through-holes has not been formed yet). When the stretched state of the stretchable sheet is released in a machine direction (a left and right direction in FIG. 7), as illustrated in FIG. 7 (a schematic view), the stretchable sheet contracts due to the contraction force of the resilient film 30. When external force is added, the stretchable sheet can stretch. Therefore, when the stretching and contracting direction of the stretchable sheet agrees with, for example, the front-back direction of a disposable diaper, the disposable diaper can stretch and contract in the front-back direction. When the stretching and contracting direction agrees with, for example, the width direction of the disposable diaper, the disposable diaper can stretch and contract in a waist or upper waist direction.

The stretchable sheet is manufactured in a manufacturing line for a product and additionally a web of the stretchable sheet is manufactured. After that, the stretchable sheet cut into a predetermined area, can be applied to a predetermined site of the product.

Typically, a sheet secured with a plurality of rubber threads in parallel is applied to a conventional disposable diaper. However, the conventional disposable diaper is disadvantageous in terms of deterioration in quality due to degradation of a hot-melt adhesive for securing to the rubber threads and the sheet as well as unstable productivity in manufacturing. The stretchable sheet can solve the problems.

Moreover, as is apparent from the contracted state in FIG. 7, regular fine wrinkles or creases are generated on the outer surface of the stretchable sheet so that a feel improves to the skin of a wearer.

Meanwhile, the first sheet layer 21 and the second sheet layer 22 are joined together with the resilient film 30 melted in the above example. In this case, there may be provided: (1) a mode in which the first sheet layer 21 or the second sheet layer 22 is joined on the surface of the resilient film 30; (2) a mode in which a surface region of the resilient film 30 melts and invades the respective fibers of the first sheet layer 21 and the second sheet layer 22 to perform the joining; and (3) a mode in which substantially the entire resilient film 30 melts and invades the respective fibers of the first sheet layer 21 and the second sheet layer 22 to perform the joining. The layer-to-layer joining mode according to the present invention, is not limited to these modes.

It can be evaluated that the first sheet layer 21 and the second sheet layer 22 are directly, namely, without the resilient film 30 interposed, joined together in the mode (3) among the modes.

In the modes (1) to (3), the melting point of the resilient film 30 is lower than the melting points of the first sheet layer 21 and the second sheet layer 22. However, the melting point of the resilient film 30 may be higher than the melting points of the first sheet layer 21 and the second sheet layer 22. In this case, a surface portion of at least one of the first sheet layer 21 and the second sheet layer 22, on the side of the resilient film 30, becomes active or melts so as to join to the resilient film 30.

Furthermore, the resilient film 30 partially may melt and additionally at least one of the first sheet layer 21 and the second sheet layer 22 may melt to perform the joining.

At least one of the first sheet layer 21 and the second sheet layer 22 may include a nonwoven fabric, and the fabric may have a core-sheath structure. In this case, for example, melting only the sheath component of the fabric melts can contribute to the joining.

In the stretchable sheet according to the present invention, the bond portion 40 are uniform in shape, size, and arrangement. In addition, the ratio of the total area of the bond portion 40 included in a unit area of the region to the unit area, namely, a joint area rate can be selected.

Figure 1:
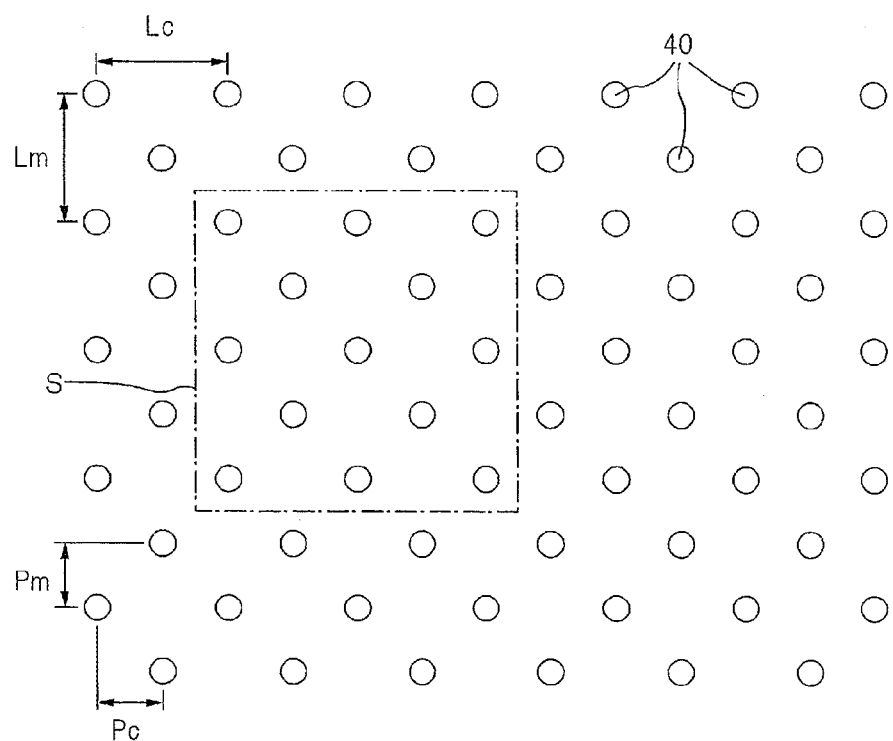
FIG. 1 is a plan view of an exemplary arrangement pattern of joints.

FIG. 1 is a plan view of an exemplary arrangement pattern of the joints (approximate to the arrangement pattern of the protruding portion group when the anvil roll is viewed in a developed state).

With reference to FIG. 1, the joint area rate in a state where the stretchable sheet has stretched up to an elastic limit in the stretching and contracting direction, includes the ratio of the total area of the bond portion 40, 40 . . . included in the unit area S, indicated in percentage. The unit area S in this case, is preferably set to a size in which ten number or more of the bond portion 40 are included (comparison is hard to perform in stretching and contracting stress with a small number). 13 number of the bond portion 40 are included in the example in FIG. 1. An outer shape for determining the unit area S may have a shape, such as a rectangle or a circle, different from a square.

The bond portion 40 each exemplarily has a circular shape as illustrated in FIG. 1. Needless to say, the shape may be elliptical or rectangular. In FIG. 1, Lm represents an arrangement interval length in the machine direction, Lc represents an arrangement interval length in an orthogonal direction orthogonal to the machine direction (a cross direction: CD), Pm represents a pitch length in the machine direction MD, and Pc represents a pitch length in the orthogonal direction (the cross direction: CD).

Figure 2:
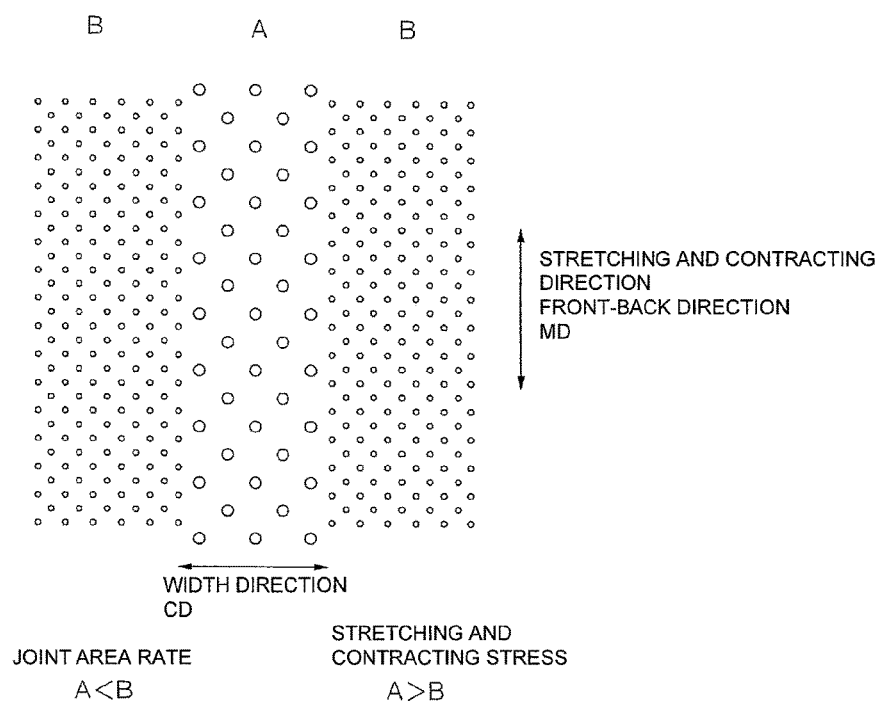
FIG. 2 is a schematic plan view of an exemplary difference in joint area rate.
Figure 3:
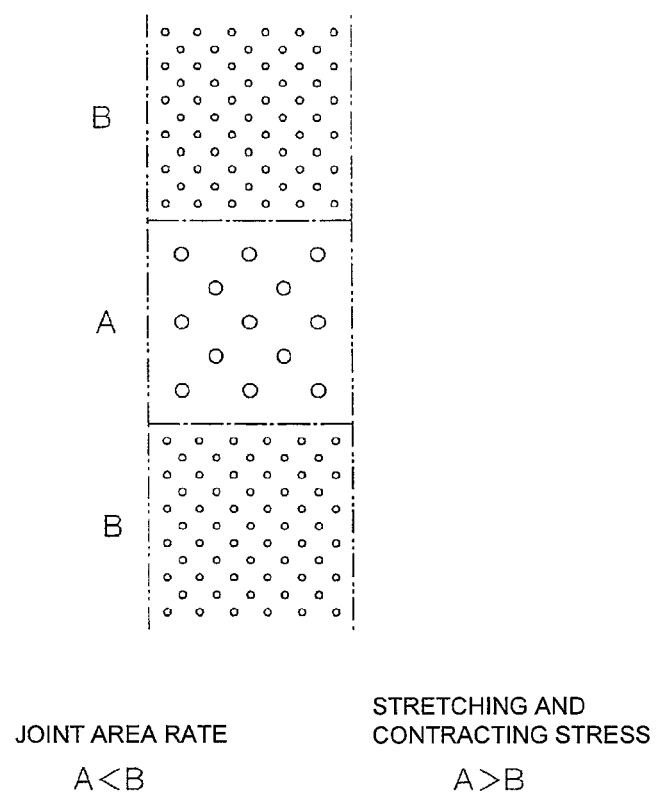
FIG. 3 is a schematic plan view of a different exemplary difference in joint area rate.
Figure 4:
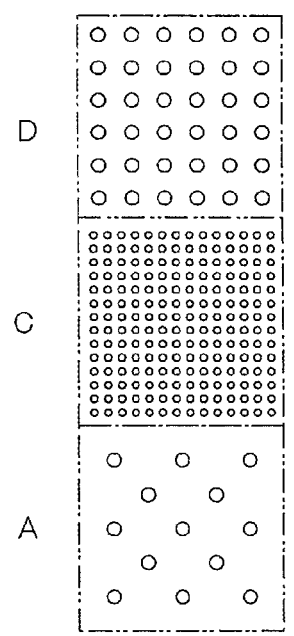
FIG. 4 is a schematic plan view of another different exemplary difference in joint area rate.
Figure 4:
Figure 5:
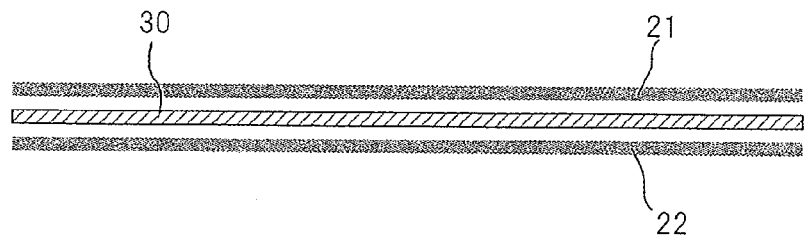
FIG. 5 is a sectional view for describing a stretchable sheet before joining.

FIGS. 2 to 4 illustrate modes in which the stretchable sheet has different joint area rates in region.

FIG. 2 illustrates the relationship between regions A and B when the following expression is satisfied in joint area rate: A<B to satisfy the following expression in stretching and contracting stress: A>B.

For example, in comparison between a case A where the pitch length Pm and the pitch length Pc are long and a case B where the pitch length Pm and the pitch length Pc are short, the case A where the pitch lengths Pm and Pc are long (a case where the joint area rate is low) is larger than the case B where the pitch lengths Pm and Pc are short (a case where the joint area rate is high) in stretch rate. As a result, the following relationship is satisfied in stretching and contracting stress: A>B.

In the mode in FIG. 2, the regions are different from each other in stretching stress in a lateral direction in FIG. 2, and thus the region A having large stretching and contracting stress is made to correspond to a center region of an absorbent article in a width direction. Then, the region B having small stretching and contracting stress (namely, small stretch and contraction) is made to correspond to both outer sides of the region A at the center.

In FIG. 3, the region B having the small stretching and contracting stress is arranged at each of the front and the rear of the region A intermediate in the front-back direction in an intermediate region. In the example, the region B and the region B at the front and the back can be made to correspond to, for example, end portions of a disposable diaper in a front-back direction. The end portions in the front-back direction are small in stretching and contracting stress and improve in shape stability so that wearing is easily made to the wearer.

According to the present invention, varying roughness and fineness in arrangement pattern or a joint area, can achieve a difference in joint area rate.

In order to understand the achievement, FIG. 4 exemplarily illustrates a region C including a number of small joints arranged, with a joint area the same as the joint area of a region D. Satisfying the following expression in joint area: A<C=D, makes the following relationship in stretching and contracting stress: A>C=D.

Figure 8:
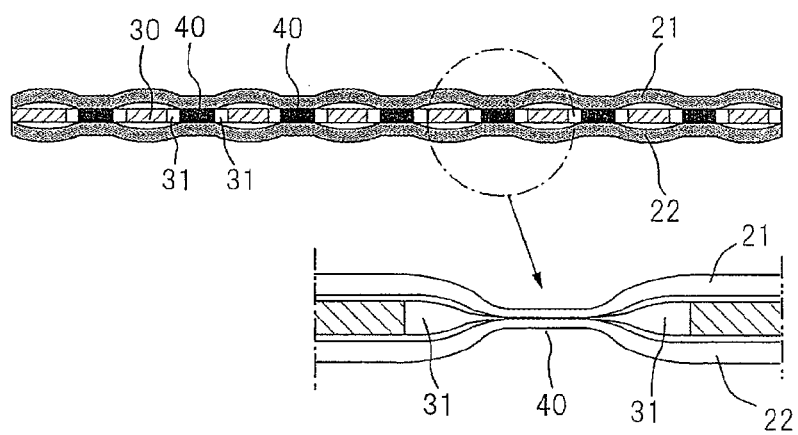
FIG. 8 is a sectional view for describing the stretchable sheet including through-holes formed in the joined state.

Physical properties, such as the thickness, material, distortion and stress characteristic, and melting point of the resilient film 30, can be appropriately selected. Selecting a relationship between the resilient film 30, the ultrasonic fusion energy to be applied to the resilient film, and the stretch rate of the resilient film 30 in manufacturing the stretchable sheet, can form a through-hole 31 around each of the bond portion 40 as illustrated in FIG. 8. In a case where the first sheet layer 21 and the second sheet layer 22 each include a nonwoven fabric, the nonwoven fabric indicates air permeability so that air permeability is indicated through the front and back of the stretchable sheet due to the formation of the through-holes 31. Therefore, in a case where the stretchable sheet is used for an outer shape sheet or exterior sheet of a disposable diaper, air permeability improves.

The reason why the through-holes 31 for the ventilation are formed is not necessarily clarified, but the ultrasonic fusion energy melts the resilient film 30 and additionally the protruding portions 60a of the anvil roll 60 presses the bond portions 40 to be a thin layer. It is considered that, at this time, a peripheral portion of each of the bond portion 40 reaches breaking strength with the resilient film 30 becoming thin and then starts breaking due to stretching and contracting stress acting on the resilient film 30 that has stretched, so that the peripheral portion contracts up to a balanced position so as to open.

Figure 13:
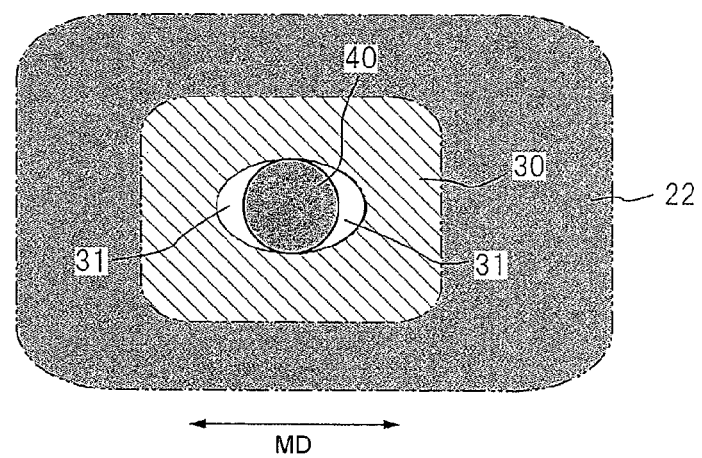
FIG. 13 is a plan view for describing exemplary formation of the through-holes.

FIG. 13 schematically illustrates exemplary formation of the through-hole 31 at one of the bond portion 40 generated in a case where the protruding portions 60a each have a circular shape. The through-hole 31 having a crescentic shape is formed on both sides of the bond portion 40 in the machine direction (a stretching direction).

Figure 14:
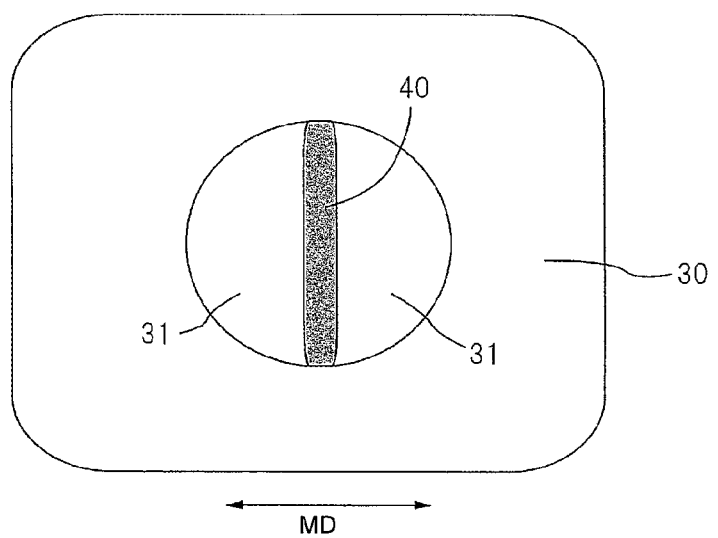
FIG. 14 is a plan view for describing exemplary formation of the through-holes in a different mode.

The bond portion 40 can be made to have an elongated shape in the direction (the cross direction: CD) orthogonal to the stretching direction (the machine direction: MD). In this case, as illustrated in FIG. 14, for example, the through-hole 31 having a semicircular shape opening large can be formed so that a suitable unit is acquired in order to increase air permeability.

Figure 15:
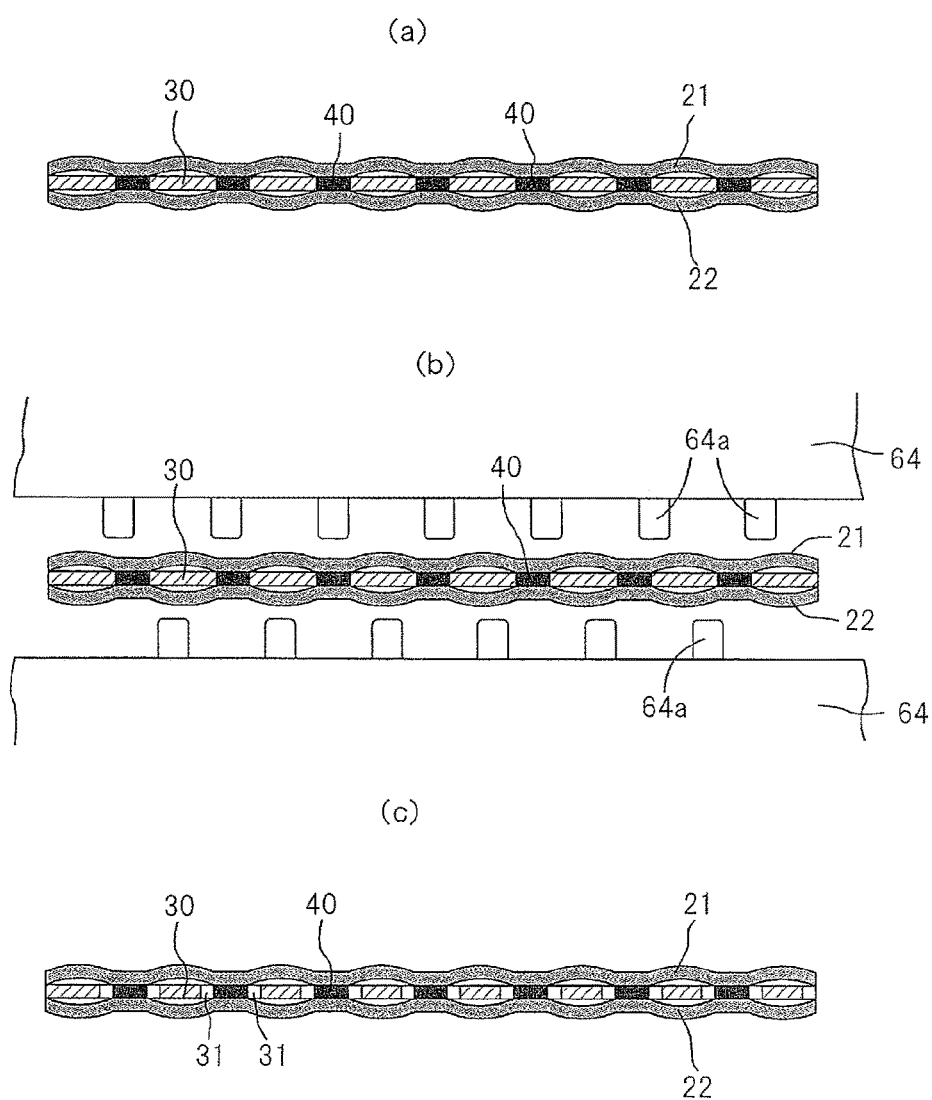
FIG. 15 is a sectional view for describing exemplary enforced formation of the through-holes.

On the other hand, the through-holes 31 are not necessarily formed to all the bond portion 40. If the through-holes 31 are required to be securely formed or to open large, a technique illustrated in FIG. 15 can be adopted.

That is, as illustrated in FIG. 15(b), the stretchable sheet including the bond portion 40 formed is inserted between a pair of rolls 64 each including elongated protrusions or projections 64a. Then, the projections 64a on one of the rolls 64 are thrust between the projections 64a adjacent on the other of the rolls 64 so that the through-holes 31 can be formed with deforming force added to the stretchable sheet.

Each bond portion 40 and through-hole 31 in shape in a natural length state, can have an arbitrary shape, such as a perfect circular shape, an elliptical shape, a polygonal shape, such as a rectangular shape (a linear shape and a rounded-corner shape included), a star shape, or a cloud shape. Each bond portion 40 is required at least to appropriately be determined in size. However, when the size is too large, influence of the bond portion 40 in hardness on a feel increases. When the size is too small, the joint area decreases and adhesion may not be sufficiently made between the materials. Thus, typically, each bond portion 40 preferably has an area of approximately 0.14 to 3.5 mm². Since the bond portion 40 is formed through the through-holes 31, the opening area of each through-hole 31 is required at least to be not less than each bond portion 40, but is preferably approximately 1 to 1.5 times the area of each of the bond portion 40.

The joints according to the present invention may make a transition directly from a main elastic portion to a non-elastic region, and additionally a transition elastic portion can be intermediately formed.

Typically, the area of each bond portion 40 and the area rate of the bond portion 40 in each region, are preferably made as follows:
(Non-Elastic Region)
Area of each bond portion 40: 0.14 to 3.5 mm² (specifically, 0.25 to 1.0 mm²)
Area rate of the bond portion 40: 16 to 45% (specifically, 25 to 45%)
(Main Elastic Portion)
Area of each bond portion 40: 0.14 to 3.5 mm² (specifically, 0.14 to 1.0 mm²)
Area rate of the bond portions 40: 1.8 to 19.1% (specifically, 1.8 to 10.6%)
(Transition Elastic Portion)
Area of each bond portion 40: 0.14 to 3.5 mm² (specifically, 0.25 to 1.0 mm²)
Area rate of the bond portion 40: 8 to 22.5% (specifically, 12.5 to 22.5%)

Figure 16:
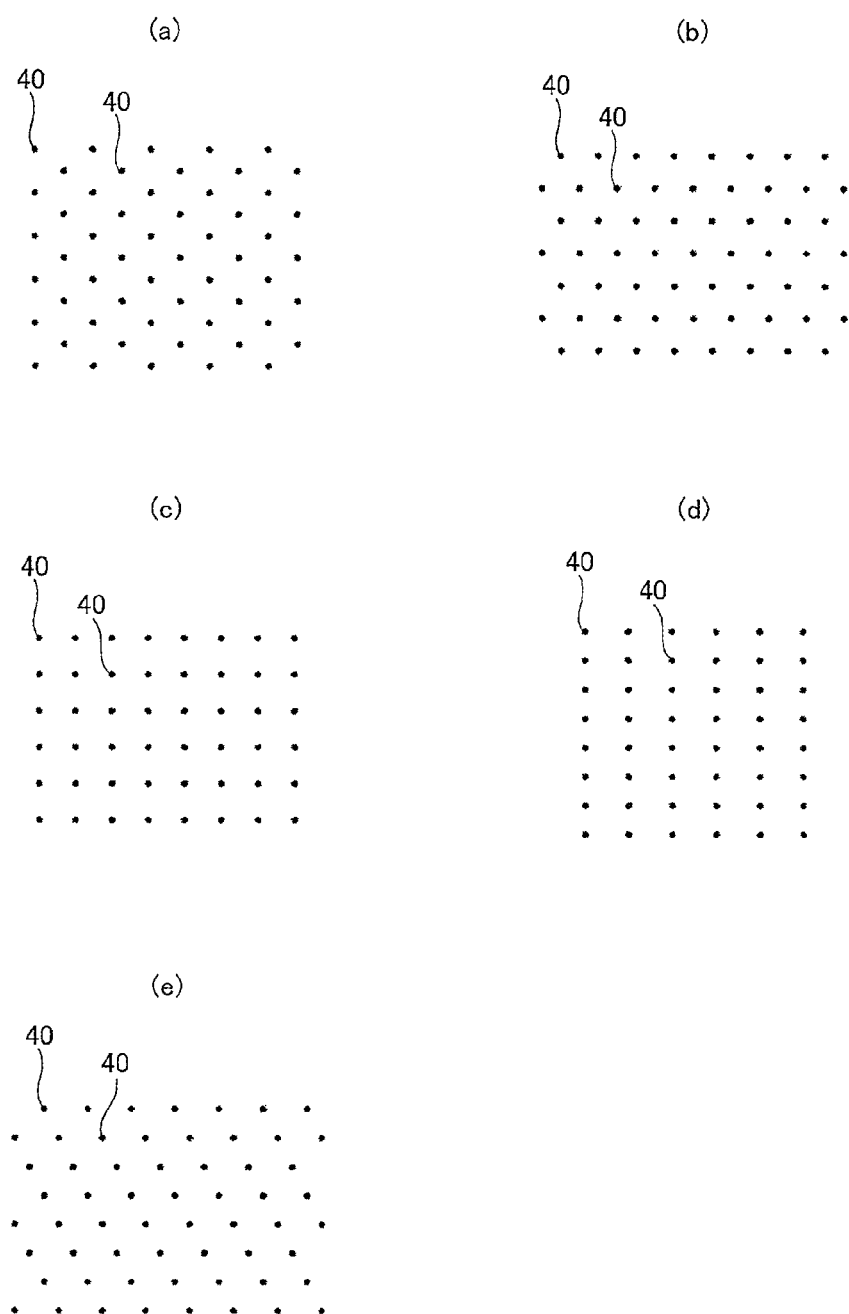
FIG. 16 is a plan view illustrating exemplary various arrangements of the joints.

The plane arrangement of the bond portion 40 and the through-holes 31 can be appropriately determined, and preferably has regular repetition. Examples of the regular repetition that can be used, include a rhombic lattice pattern as illustrated in FIG. 16(a) and a hexagonal lattice pattern as illustrated in FIG. 16(b) (each referred to as a staggered pattern), a tetragonal lattice pattern as illustrated in FIG. 16(c), a rectangular lattice pattern as illustrated in FIG. 16(d), a parallelogrammic lattice pattern as illustrated in FIG. 16(e) (as illustrated, a mode in which two groups each including a number of parallel lines in an oblique direction, are provided, the two groups crossing each other) (a mode in which the groups each incline at an angle of less than 90° to the stretching and contracting direction, included), and groups of the bond portion 40 regularly repeated (an arrangement per group may have a regular pattern or an irregular pattern, or a design or a character). The arrangement mode of the bond portion 40 and the through-holes 31 can remain the same or can vary in the main elastic portion, the transition elastic portion, and the non-elastic region.

The resilient film 30 is not particularly limited, and a resin film required at least to have its own elasticity, can be, but not particularly limited, used. A blend including at least one of thermoplastic elastomers, such as a styrene elastomer, an olefin elastomer, a polyester elastomer, a polyamide elastomer, and a polyurethane elastomer, processed to have a film shape by extrusion molding, such as a T-die method or an inflation method, can be used. In addition to a nonporous film, a film including a number of holes or slits formed for ventilation, can be used for the resilient film 30. In particular, the resilient film 30 preferably has a tensile strength of 8 to 25 N/35 mm in the stretching and contracting direction, a tensile strength of 5 to 20 N/35 mm in the direction orthogonal to the stretching and contracting direction, a tensile elongation of 450 to 1050% in the stretching and contracting direction, and a tensile elongation of 450 to 1400% in the direction orthogonal to the stretching and contracting direction. Note that, except that a test piece has a rectangular shape measuring 35 mm wide by 80 mm long and a tensile testing machine (e.g., AUTOGRAPHAGS-G100N manufactured by SHIMADZU Corporation) is used, the tensile strength and the tensile elongation (breaking elongation) indicate values measured with an initial chuck interval of 50 mm and a tensile speed of 300 mm/min conforming to JIS K7127: 1999 "Plastics-Determination of tensile properties". The thickness of the resilient film 30 is not particularly limited, but is preferably approximately 20 to 40 μm. The basis weight of the resilient film 30 is not particularly limited, but is preferably approximately 30 to 45 g/m$^2$, and particularly preferably approximately 30 to 35 g/m$^2$.

<Glossary in Specification>

The terms in the specification below have the following meanings unless otherwise described in the specification.

The "stretch rate" means a value based on the natural length defined as 100%.

The "basis weight" is measured as follows: A sample or a test piece is preliminarily dried and then is retained into a laboratory or into a device in a reference condition (the temperature and the relative humidity in an experimental area are 20±5° C. and 65% or less, respectively) so as to have a constant weight. The preliminary drying means that the sample or the test piece is made to have the constant weight in an environment in which the relative humidity is not out of 10 to 25% and the temperature does not exceed 50° C. Note that, fibers having an official regain of 0.0% are not required to be preliminarily dried. A sample having dimensions of 200 mm×250 mm (±2 mm) is cut out from the test piece that has had the constant weight, with a cutting template (200 mm×250 mm, ±2 mm). The weight of the sample is measured and then is multiplied by 20 so that the weight per square meter is calculated to be as the basis weight.

In a case where no environmental conditions have described in experiment and measurement, the experiment and the measurement are performed in the laboratory or in the device in the reference condition (the temperature and the relative humidity in the experimental area are 20±5° C. and 65% or less, respectively).

INDUSTRIAL APPLICABILITY

The stretchable sheet according to the present invention can be used for absorbent articles in general each having a stretchable structure, examples of the absorbent articles including various disposable diapers, such as an underpants-type disposable diaper, a tape-type disposable diaper, and a pad-type disposable diaper, and a sanitary napkin.

With joining being performed in a manufacturing line for an absorbent article, the stretchable sheet according to the present invention can be manufactured as a sheet included in the back of the absorbent article.

REFERENCE SIGNS LIST

A to D regions
21 first sheet layer
22 second sheet layer
30 resilient film
31 through-hole
40 bond portion
60 anvil roll
61 ultrasonic horn
63 counter roll (nip roll)

The invention claimed is:

1. A method of manufacturing a stretchable sheet that stretches and contracts, the method comprising:
   interposing a resilient film that stretches and contracts, in a stretched state between a first sheet layer having no elasticity and a second sheet layer having no elasticity; and
   joining the first sheet layer and the second sheet layer together with a number of joints directly or through the resilient film by melting the resilient film with ultrasonic fusion energy applied by a thermal fusion device from an outside of the first sheet layer and an outside of the second sheet layer to a number of joint regions with intervals, in a state where the resilient film has been interposed in the stretched state between the first sheet layer and the second sheet layer, during the interposing,
   wherein the thermal fusion device includes an anvil roll and an ultrasonic horn,
   the anvil roll includes a number of protruding portions formed with intervals in a roll length direction and in an outer circumferential direction on an outer surface,
   a counter roll is arranged to face the anvil roll, and
   the resilient film is supplied around the counter roll so as to be supplied around the anvil roll, and the anvil roll is accelerated to be faster than the counter roll in peripheral speed to stretch the resilient film and additionally a group of the protruding portions of the anvil roll and the ultrasonic horn performs the joining.

2. The method of manufacturing the stretchable sheet according to claim 1, wherein a through-hole is formed through at least a boundary portion in a direction of the stretching between the resilient film and each of the joints, with the first sheet layer and the second sheet layer retained, no hole being formed over the entirety of each of the joint regions, during the joining.

3. The method of manufacturing the stretchable sheet according to claim 1, wherein the counter roll is a nip roll which constitutes a nip stage together with the anvil roll, and
   the resilient film is supplied around the anvil roll through the nip stage.

4. The method of manufacturing the stretchable sheet according to claim 3, wherein a distance between the nip stage and a position at which the resilient film separates from the anvil roll, is 250 mm or less.

5. The method of manufacturing the stretchable sheet according to claim 1, wherein the counter roll is a nip roll which constitutes a nip stage together with the anvil roll, and
   the resilient film is supplied around the anvil roll through the nip stage.

6. The method of manufacturing the stretchable sheet according to claim 1, wherein the anvil roll is a crowned roll.

7. The method of manufacturing the stretchable sheet according to claim 1, wherein a protruding portion area rate of a total area of the group of the protruding portions included in a unit area, varies at least in roll length when the anvil roll is viewed in a developed state.

* * * * *